United States Patent [19]

Kere et al.

[11] Patent Number: 5,556,786
[45] Date of Patent: Sep. 17, 1996

[54] ANHIDROTIC ECTODERMAL DYSPLASIA GENE AND METHOD OF DETECTING SAME

[75] Inventors: Juha Kere, Helsinki, Finland; David Schlessinger, University City, Mo.; Albert de la Chapelle, Helsingfors, Finland

[73] Assignee: Washington University, St. Louis, Mo.

[21] Appl. No.: 52,997

[22] Filed: Apr. 27, 1993

[51] Int. Cl.$^6$ .......................... C12N 15/00; C07H 21/04
[52] U.S. Cl. ....................... 435/320.1; 536/23.5
[58] Field of Search ........................ 435/172.3, 6, 320.1; 536/23.5

[56] References Cited

U.S. PATENT DOCUMENTS 4,889,806  12/1989  Olson et al. .................... 435/172.3

OTHER PUBLICATIONS

Lafraniere et al. Genomics 11. 352–363 (1991) "Physical Mapping of 60 DNA Markers in the p21.1–q21.3 region of Human X Chromosome".
Sambrook, J. et al. "Molecular Cloning"–A Laboratory Manual Published by Cold Spring Harbor Lab. Press 1989 pp. 2.9 & 2.10.
Mandel et al., "Genome Analysis and the Human X Chromosome," *Science* 258:103–109 (1992).
Zonana et al., "Detection of a Molecular Deletion at the DXS732 Locus in a Patient With X–linked Hypohidrotic Extodermal Dysplasia (EDA), With the Identification of a Unique Junctional Fragment, " *Am. J. Hum. Genet.* 52:78–84 (1993).
Zonana et al, "High–resolution Mapping of the X–linked Hypohidrotic Ectodermal Dysplasia (EDA) Locus, " *Am. J. Hum. Genet.* 51(5) :1036–46 (1992).
Zonana et al., "Prenatal Diagnosis of X–linked Hypohidrotic Ectodermal Dysplasia by Linkage Analysis," *Am. J. Genet.* 35(1) :132–5 (1990).
Goodship.et al., "Possible Genetic Heterogeneity in X linked Hypohidrotic Ectodermal Dysplasia," *J. Med. Genet.*27(7): 422–25 (1990).
Blecher et al., "Induction of Sweat Glands by Epidermal Growth Factor in Murine X–linked Anhidrotic Ectodermal Dysplasia," *Nature*345(6275) :542–44 (1990).
Kere et al., "Cloning of the Anhidrotic Ectodermal Dysplasia Gene: Identification of Candidate mRNAs Associated With CpG Islands Near Translocation Breakpoints in Two Female Patients,"presented at 4th X–Chromosome Workshop, St. Louis, MO, May 9–12, 1993.
Thomas et al., "Molecular Identification of the X–Chromosomal Breakpoints in Two Isolated Female Patients Who Express X–Linked Hypohidrotic Ectodermal Dysplasia (EDA) and an interstital Deletion in a Second EDA Male," presented at 4th X–Chromosome Workshop, St. Louis, MO, May 9–12, 1993.

*Primary Examiner*—Charles L. Patterson, Jr.
*Assistant Examiner*—Lisa J. Hobbs
*Attorney, Agent, or Firm*—Popham, Haik, Schnobrich & Kaufman, Ltd.

[57] ABSTRACT

The present invention relates to various yeast artificial chromosomes (YACs) which contain all or a portion of the human EDA gene for anhidrotic ectodermal dysplasia, probes specific for human EDA gene and methods of diagnosis of EDA gene-related disorders.

5 Claims, 4 Drawing Sheets

ANHIDROTIC ECTODERMAL DYSPLASIA GENE AND METHOD OF DETECTING SAME

This invention was made with government support under HG00247 grant awarded by the National Institutes of Health. The Government has certain rights in the invention.

BACKGROUND OF THE INVENTION

1. Field of the Invention

This invention relates to the human anhidrotic ectodermal dysplasia (EDA) gene code for anhidrotic ectodermal dysplasia, an X-chromosomal recessive disorder. More particularly, the invention relates to various yeast artificial chromosomes (YACs) which contain all or a portion of the human EDA gene and to methods for making the same.

2. Description of the Prior Art

Physical maps of large chromosomal regions are defined by a series of DNA markers, preferably at closely and evenly distributed intervals. Such maps can be developed without cloning most of the chromosomal DNA, but it is advantageous to clone DNA in order to identify genes and study gene expression. Therefore, physical maps are preferably produced by reassembling chromosome equivalents from purified DNA.

The DNA molecule that makes up the X chromosome is much too large to be handled intact, so it must be broken into cloned fragments that are arranged by overlaps to create a contiguous map of the DNA. Larger clones, such as yeast artificial chromosomes (YACs), make physical mapping easier.

Two methods may be used to organize DNA fragments into a mapped region. In the first method, chromosome-specific probes are used to screen YAC libraries for cognate clones. Many such probes have been characterized and genetically or cytogenetically assigned to regions of the X chromosome. Probes defining genetically mapped, polymorphic loci are used to find corresponding larger YAC clones and provide markers that format the physical map. Such probes may be obtained as clones (in plasmids, phage, or cosmids) derived from flow-sorted chromosomes or genomic libraries constructed from somatic cell hybrids; by polymerase chain reaction (PCR)-based amplification of microdissected fragments of individual chromosomes; or by amplification of segments flanked by human-specific interspersed, repetitive sequences present in hybrid cells and YACs.

In the second method, clones for all or part of a chromosome are systematically analyzed by fingerprinting techniques, such as sizing restriction fragments or studying fragments that contain certain repetitive sequences. Overlaps between clones are then detected by computer analysis.

Two types of YAC libraries can be used to build an X physical map: total genomic libraries or X chromosome-specific libraries constructed from appropriate somatic hybrids. Chromosome-specific libraries have a smaller number of clones, and so favor screening with probes.

Because of the functional hemizygosity of the X chromosome, many translocations between X and an autosome as well as other structural abnormalities (such as deletions, duplications, and isochromosomes) are detected clinically. By means of the selectable markers described above, such rearranged chromosomes have been isolated in somatic cell hybrids and have provided a rich resource for interval mapping, especially in the pericentromeric region and in the middle and distal long arm regions.

At least 16 X-linked diseases have been cloned on the basis of prior knowledge of a defective protein. However, for most of the remaining diseases, the bio-chemical defect is unknown or very uncertain and it is necessary to use mapping strategies to identify the genes corresponding to the diseases.

Fortunately, X-linked diseases have features that facilitate positional cloning. Chromosomal assignment, which can be difficult to determine for rare autosomal diseases, is obvious for X-linked diseases because of the inheritance pattern. Rare affected females with balanced X-autosome translocations have been found for about 10 diseases. In these patients, the normal X chromosome is generally inactive, and the translocated X active, because of a selection process operating in early embryogenesis against cells carrying an inactive translocated X. Translocations that have a breakpoint within a gene will lead to expression of the corresponding disease, as the uninterrupted copy on the normal X is inactive. Such translocations have provided precise localization for the relevant disease genes that could be confirmed by linkage analysis in affected families and have been instrumental in the cloning of several genes (Mandel et al. 1992).

Anhidrotic (hypohidrotic) ectodermal dysplasia (EDA; Christ-Siemens-Touraine syndrome; CST syndrome; MIM 305100, McKusick 1990) is an X-linked recessive disorder linked with the absence or hypoplasia of hair, teeth, and sweat glands as main manifestations (Reed et al. 1970, Clarke 1987). Prenatal diagnosis of X-linked anhidrotic ectodermal dysplasia (EDA) was previously performed by the direct histological analysis of fetal skin obtained by late second trimester fetoscopy (Zonana et al. 1990). Zonana et al. report that recent gene mapping of the locus for the EDA gene to the region of Xq11-21.1 permits indirect prenatal diagnosis of the disorder by the method of linkage analysis, based on closely linked marker loci, during the first trimester of pregnancy.

The EDA gene has been mapped to Xq12-q13 by genetic linkage analysis using restriction fragment length polymorphisms (RFLP) markers (MacDermot et al. 1986, Kolvraa et al. 1986, Clarke et al. 1987, Hanauer et al. 1988, Zonana et al. 1988a). However, Goodship et al. report a family with anhidrotic ectodermal dysplasia in which the disease did not segregate with the Xq11-q13 region of the X chromosome, as expected (Goodship et al. 1990). Physical and linkage maps for the pericentromeric region of the X chromosome have been refined (Lafreniere et al. 1991, Jones et al. 1991), but the region in which the EDA gene resides has not previously been cloned.

A similar syndrome with anhidrosis and absence of sweat glands is known in the mouse, in which the mutant gene is called Tabby (Ta) (Blecher 1986). Consistent with the map position in man, the Ta gene has been mapped in syntenically corresponding region in the X chromosome of mouse (Brockdorff et al. 1991). Blecher et al. report that epidermal growth factor (EGF) induces development of dermal ridges and functional sweat glands in Ta/Y hemizygotes, indicating a role in mammalian morphogenesis and possible treatment of anhidrotic ectodermal dysplasia (Blecher et al., 1990).

Zonana et al. have defined the human DXS732 locus by a conserved mouse probe pcos169E/4 (DXCrc169 locus) that co-segregates with the mouse tabby (Ta) locus, a potential homologue to the EDA locus. Zonana et al. report that the absence of recombination between EDA and the DXS732 locus supports the hypothesis that the DXCrc169 locus in the mouse and the DXS732 locus in humans may contain candidate sequences for the Ta and EDA genes, respectively (Zonana et al. 1992)

Zonana et al. further disclose the genetic nature of this anhidrotic ectodermal dysplasia. More particularly, they have screened a panel of genomic DNA samples from 80 unrelated males with EDA and identified a single individual partially deleted at the DXS732 locus. The individual has the classical physical signs and symptoms of EDA, has no other phenotypic abnormalities, and does not have a cytogenetically detectable deletion in the Xq12-q13.1 region. Zonana et al. conclude that since the DXS732 locus contains a highly conserved sequence in both the mouse and the hamster, it must be considered as a candidate locus for the EDA gene (Zonana et al. 1993).

Thomas et al. disclose two female patients who express the full clinical spectrum of anhidrotic ectodermal dysplasia in association with different X-chromosome cyotogenetic rearrangements. Both patients have cytogenetic breakpoints within the Xq13.1 region. A probe derived from cell lines from the two patients was used to screen a panel of unrelated affected EDA males and identified a patient with an interstitial deletion (Thomas et al. 1993).

While none of the prior art have succeeded in isolating the EDA gene, cloning of the region in which the EDA gene resides would have practical benefits. These would include both the development of tests for clinical variants in the gene and applications to the study and control of optimal hair, tooth, skin, and sweat gland development, all of which require a functional EDA gene.

Therefore, it is desirable to further limit the segment of DNA that contains the human EDA gene and to provide various yeast artificial chromosomes (YACs) which contain all or a portion of the human EDA gene and specific probes for the human EDA gene sequences.

SUMMARY OF THE INVENTION

Using available DNA markers and somatic cell hybrids, X-chromosomal breakpoints were mapped in two translocations involving bands Xq12-q13 in female EDA patients. The breakpoints were further mapped within a yeast artificial chromosome contiguous sequence constructed by chromosome walking techniques. Genomic DNA markers were recovered which map between the two translocation breakpoints, representing putative portions of the human EDA gene.

The invention provides a cloning vector containing all or a portion of a DNA sequence encoding human EDA gene sequences. Also provided is a vector capable of expressing human EDA gene sequences in cell cultures, including fibroblasts and keratinocytes.

The invention further provides a DNA segment which encodes for the human EDA gene.

In another preferred embodiment of the invention, the invention provides a kit for the diagnosis of diseases associated with X-linked anhidrotic ectodermal dysplasia that comprises a cloning vector containing all or a portion of a DNA sequence encoding human EDA gene. Preferably, the cloning vector comprises fragments of yeast artificial chromosome which are cloned in plasmids, bacteriophages, cosmids, or similar vectors containing all or a portion of a DNA sequence encoding the human EDA gene.

The invention further provides a group of overlapping yeast artificial chromosomes whose combined content is about 1.2 Mb and spans from DXS135 to markers distal of DXS339, covering two translocation points in the human EDA gene.

BRIEF DESCRIPTION OF THE DRAWINGS

The invention is better understood by reading the following Detailed Description of the Invention with reference to the accompanying drawing figures, in which.

DETAILED DESCRIPTION OF THE INVENTION

Figure 1:
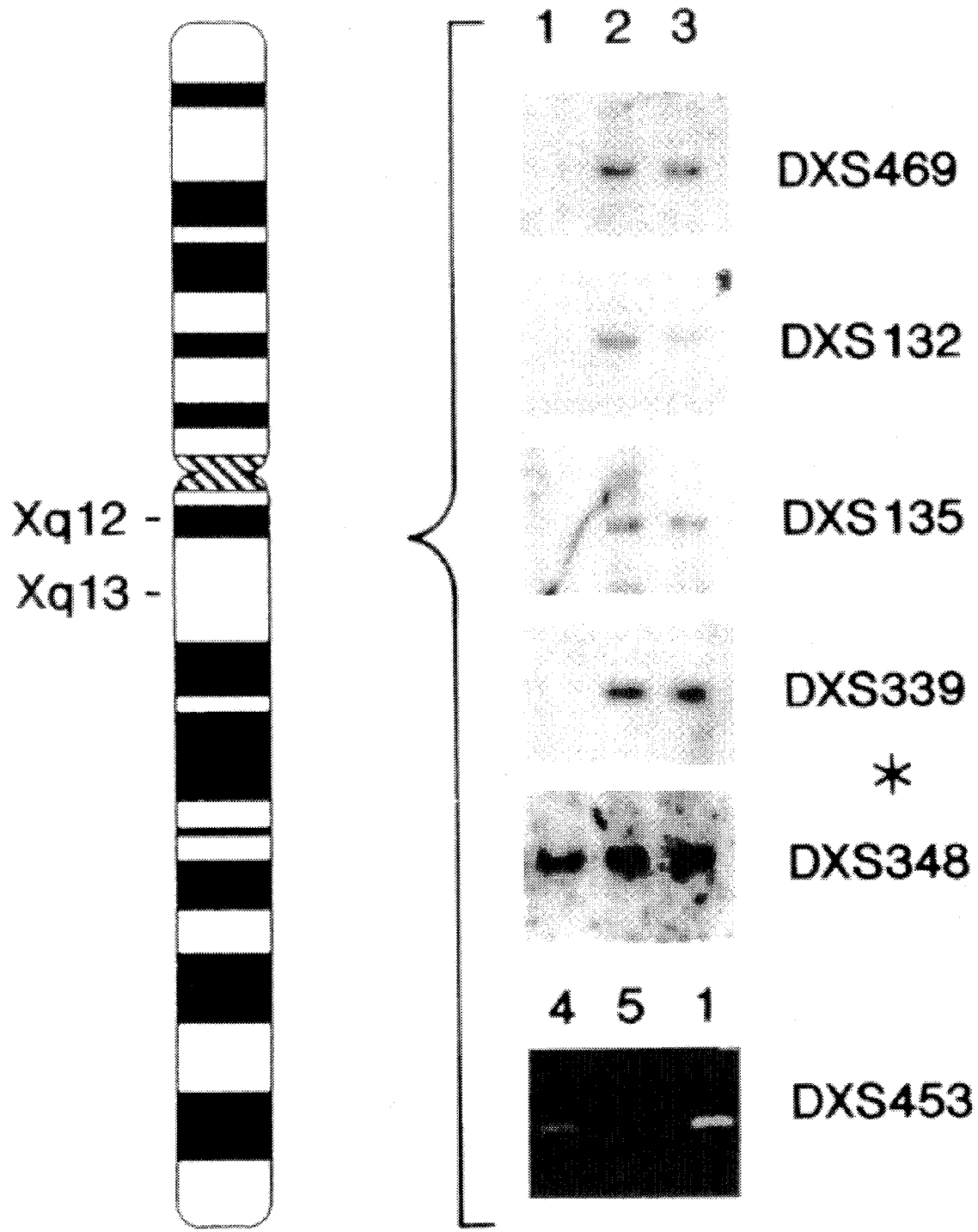
FIG. 1 illustrates mapping of the X chromosomal breakpoint in a patient.

The EDA gene is believed to interrupt a relatively early developmental pathway, since clinical signs of EDA are confined to tissues arising from one developmental layer, the ectoderm (Clarke 1987, Söderholm et al. 1985). In EDA, histopathology of the skin shows both reduced numbers and defective maturation of hair and sebaceous, apocrine, and eccrine glands (Reed et al. 1970). These structures all derive from the embryonal basal cell layer, first become apparent during the third to fourth gestational month, and continue to develop until birth (Serri et al. 1962, Hashimoto 1970). Knowledge of the molecular defect in EDA should allow a further dissection of steps in ectodermal development as well as in the pathogenesis of EDA.

Anhidrotic ectodermal dysplasia in its fully expressed form is rare in women, although varying degrees of signs may be present in gene carriers. Full expression of the disease in the translocation patient may be due to the disruption of the EDA gene in the translocated chromosome and the preferential inactivation of the structurally normal X chromosome which most likely carries a normal allele for the EDA gene. Disruptions of the EDA gene which may cause full expression of anhidrotic ectodermal dysplasia include, but are not limited to, translocations, point mutations, deletions, insertions, breakage points, and other chromosomal defects.

The present technique used to identify the EDA gene has been based on the use of translocation breakpoints to define the localization of the gene and the recovery of yeast artificial chromosome (YAC) clones from the region using previously available linkage markers and unique new markers developed by the present inventors.

The present invention has unexpectedly identified two gene translocations that interrupt the EDA gene. While the exact mode of action of the gene is unknown, it is believed that several possibilities would explain the abrupt suspension of skin and/or hair cell development as well as sweat gland cell development. One possibility is that the gene is a receptor gene located on cell surfaces, or a signal-transducing molecule functionally associated with a cell surface receptor, and in its absence or modified form it interrupts normal cell development. Another possibility is that the EDA gene may form a new and yet unknown growth factor which induces development of skin, hair, and the sweat glands. Accordingly, identification of the EDA gene could play a crucial role as a candidate involved in the development of skin, hair, and sweat gland cell growth.

Three female patients have been reported who have different X;autosome translocations involving chromosomal band Xq12-q13 (Cohen et al. 1972, Zonana et al. 1988b, Turleau et al. 1989, MacDermot and Hulten 1990, Limon et al. 1991). By analogy with other X chromosomal diseases such as chronic granulomatous disease, Duchenne muscular dystrophy, fragile X syndrome, choroideremia, and Kallmann syndrome, these translocations very likely disrupt the EDA gene and thus provide unique physical landmarks to localize it. Such markers have allowed recovery of the region around the translocation breakpoints in yeast artificial chromosomes and identify genomic DNA segments located between the breakpoints, most likely including portions of the EDA gene. They have also provided probes to recover the coding regions of the EDA gene.

Clinical and cytogenetic findings in one patient identified as patient "AK" with translocation t(X;1)(q13.1;p36.3) have been described (Limon et al. 1991). A lymphoblastoid cell line was established and used as a source for high molecular weight DNA. Somatic cell hybrids were constructed by fusing "AK" fibroblasts with hypoxanthine phosphoribosyltransferase deficient mouse cells (RAG). Methods for cell fusion, hybrid selection, and cytogenetic characterization of clones have been described previously (Grzeschik 1976, Grzeschik 1980). After initial characterization, one of the hybrid clones (AKRAG9) retaining translocated fragments of the human X chromosome but no cytogenetically evident intact X chromosome was used to identify genomic DNA segments.

The somatic cell hybrid ALR-1-BSH-6 constructed from a second patient identified as patient "AnLy" was obtained. Patient "AnLy" had a t(X;9)(q13.1;p24) associated with EDA; her clinical and cytogenetic findings have been described (Cohen et al. 1972, MacDermot and Hulten 1990). The ALR-1-BSH-6 cell line contains the der(9) chromosome including the distal portion of Xq in more than 90% of mitoses, and the cytogenetically normal X in less than 10% of mitoses. The presence of the normal X chromosome in some cells gives rise to weakly positive signals for all X chromosomal PCR assays on ALR-1-BSH-6 DNA.

The "X only" and X3000 somatic cell hybrid DNAs were used as controls; their sources and use in the testing of PCR assays have been described (Kere et al. 1992).

Terms as Used Herein

The term "probe" as used herein refers to any biomolecule that binds to some specific target molecule and bears a chemical label that can be traced after binding has occurred, including but not limited to an oligo- or polynucleotide, protein, lipid, or polysaccharide.

The term "vector" as used herein refers to any RNA or DNA that can be linked to a nucleic acid segment from a heterologous source and used for cloning the foreign nucleic acids in a host, including but not limited to yeast artificial chromosomes, plasmids, phages and cosmids.

The term "plasmid" as used herein refers to a type of cloning vector comprising small, circular, duplex DNA molecules.

The term "cDNA" as used herein refers to single-stranded complementary DNA that is copied from mRNA by the enzyme reverse transcriptase.

The term "DNA polymerase I" (POL I) as used herein refers to an enzyme that, using a DNA strand as a template, catalyzes the synthesis of a complementary DNA strand from dNTPs.

The term "DNase I" as used herein refers to an enzyme that catalyzes the formation of single-stranded breaks at random sites along a segment of single- or double-stranded DNA.

The terms "dNTPs" and "NTPs" as used herein refer to the four deoxyribonucleotide triphosphates (dATP, dCTP, dGTP, and dTTP) and ribonucleotide triphosphates (ATP, CTP, GTP, and UTP), respectively.

The term "oligonucleotide" as used herein refers to a short strand of DNA or RNA ranging in length from about 2 to about 30 bases.

The term "peroxidase" as used herein refers to any of a class of enzymes that catalyzes the reduction of a peroxide, including but not limited to horseradish peroxidase.

The term "phosphoramidite" as used herein refers to a chemically modified nucleotide containing an activated phosphoester group at the 3' carbon and a dimethoxytrityl (DMT) blocking group at the 5' end.

DNA Probes and Sequence-tagged Sites

DNA probes for loci DXS132, DXS135, DXS159, DXS339, DXS348, and DXS469 have been described (for references and original sources, see Davies et al. 1991 and Lafreniere et al. 1991). Probes cpX289, cpX23, cpX93, pRX21H3a, pRX97H5, and cpX58 were obtained for loci DXS159, DXS132, DXS135, DXS339, DXS348, and DXS469, respectively. The following human X chromosomal probes were isolated during the course of the study by ligation-mediated polymerase chain reaction (PCR) recovery of YAC insert ends: yWXD1319-L, yWXD4093-L, yWXD1320-L, yWXD5218-R, and yWXD1261-R. Throughout the text, insert ends are named L (for left, closer to the large or centromeric arm of the vector pYAC4) and R (for right, closer to small arm).

PCR assays for DXS453 (Weber et al. 1990) and CCG1 (Kere et al. 1992) have been described. Primers for the randomly derived sequence-tagged site (STS) sWXD178 were GTTAATAGTAATGTCCTCTCTTTC (SEQ ID NO: 1) and ACCTTTAGTTAGATTGATGAAGCC (SEQ ID NO: 2), yielding an 82 bp product.

Parts of probes cpX289, pRX21H3a, and pRX97H5 and insert ends of YACs were sequenced directly from PCR products and primers were designed. The primer sequences for these STS's are as follows (product size in parentheses): DXS159, CAAGGAAAGGGATTGGCAAG (SEQ ID NO: 3) and AGACCCGAGAGAGCAATTAG (SEQ ID NO: 4) (239 bp); DXS339, GAACAGGTTATGGGAGGGG (SEQ ID NO: 5) and GATCTGGAAAGATGAGCTGAG (SEQ ID NO: 6) (158 bp); DXS348, TCTTGTATCCCTTTGCTTACTG and (SEQ ID NO: 7) CATTTGCCCAACTTACTAAACCAC (SEQ ID NO: 8) (115 bp); yWXD4093-L, GGCAGTTCCAGTAAAATGCAGAC (SEQ ID NO: 9) and GGAGCTGAGGCCAAGGAG (SEQ ID NO: 10) (77 bp); yWXD1320-L, GCTGCAAAATTATTGTTGCTGTGG (SEQ ID NO: 11) and AACAAGATCGTGAAACAGGATG (SEQ ID NO: 12) (60 bp). Due to the partially repetitive nature of DXS339 sequence, the primers were used at molar ratio of 10:1 to yield less background signal; all other primers were used at equimolar concentrations. Additional novel sequences have been identified and include the following primer sequences:

a) GGCAGTTCCAGTAAAATGCAGAC (SEQ ID NO: 9);

b) GGAGCTGAGGCCAAGGAG (SEQ ID NO: 10);

c) GCTGCAAAATTATTGTTGCTGTGG (SEQ ID NO: 11);

d) AACAAGATCGTGAAACAGGATG (SEQ ID NO: 12);

e) GGTTGTATGGCCTTAGACTC (SEQ ID NO: 13);

f) GTGGTGCTGGGGAATAGTG (SEQ ID NO: 14);

g) TCTGTCCTCTCCTGCCATC (SEQ ID NO: 15);

h) AATAAAGCCTCCTGCCTCCTG (SEQ ID NO: 16);

i) ATTTCCTACCACTCCACCC (SEQ ID NO: 17);
j) CTTGAGATTTGAAGAGAGCCC (SEQ ID NO: 18);
k) ACCACTCCACCCCTTATTC (SEQ ID NO: 19);
l) GACAGAGGTATCAGAAAGTCAAA (SEQ ID NO: 20);
m) CCAGACCTATGAATGCAAAC (SEQ ID NO: 21); and
n) GTGAATAATAGCACTTCTGCC (SEQ ID NO: 22).

PCR assays for all STS's can be performed under standard conditions. One exemplary PCR method involves the following conditions: preheating at 94° C. for 150 seconds, followed by 35 cycles at 94° C. for 30 seconds, 55° C. for 45 seconds, 72° C. for 45 seconds in a Perkin-Elmer PCR machine. Reaction mixtures (10 ul) contained 100 mMKCl, 10 mM Tris-HCl pH 8.6, 1.5 mM $MgCl_2$, 5 mM $NH_4Cl$, 125 uM dNTP, 4 pmol of each primer, and 0.25 U AmpliTaq (Cetus). Reaction products were analyzed in 1.5–3% agarose gels.

Yeast Artificial Chromosome Clones, End-fragment Isolation, and Subcloning

Traditional cloning methods, such as those using plasmid, bacteriophage, or cosmid vectors, are limited by the size of the inserts that they carry. Using these types of vectors, clonable segments reach their upper limit at a size of about 50 kb of DNA. Yeast artificial chromosomes are a new type of vector capable of carrying inserts of more than one thousand kb-pairs in length (Steinberg et al. 1993).

YAC clones were recovered using PCR assays for DXS339, DXS348, DXS453, yWXD4093-L, yWXD1320-L, and sWXD178. The construction of YAC contigs proceeded with three independently prepared libraries, two of which were enriched for X chromosomal clones. The following YAC libraries were screened, yielding the number of YACs indicated in parentheses: a human genomic library constructed from normal male DNA (3 YACs); a human genomic library constructed from cells with karyotype 49, XXXXX (12 YACs); and a library constructed from somatic cell hybrids containing only human Xpter-q27 (Lee et al. 1992) (10 YACs).

It was found that the construction of YAC contigs was hampered by the repetitive nature of some loci used as markers. In particular, several YAC pools gave false positive signals for two different primer pairs for DXS339; a cross-hybridizing sequence was identified close to DXS159, located less than a megabase proximal to the EDA region.

It was unexpectedly found possible to construct two contigs spanning altogether approximately 1.5 Mb and linking up loci whose physical distances had not been determined previously. The contig data agree with the order of probes as previously determined (Lafreniere et al. 1991; Jones et al. 1991) and should allow more detailed mapping of the region. The maximum distance between loci DXS135 and DXS339 is 269 kb, and the interval from DXS453 to DXS348 is less than 280 kb.

Sizes of YACs were determined by pulsed field gel electrophoresis (PFGE) using DNA prepared in agarose beads. Restriction maps were obtained by hybridizing YAC vector-specific and internal probes to blots of fully and partially digested DNA samples separated by PFGE.

To subclone YAC DNA, yeast DNA was digested partially with Sau3AI and separated in 0.5% low melting point agarose gel. Digestion products of approximately 15–25 kb were excised from the gel and recovered by phenol extraction and isopropanol precipitation. An aliquot was ligated to 1 ug BamHI-digested and dephosphorylated EMBL3 vector (available from Stratagene Inc.) overnight in 10 ul reaction. Recombinant phage were packaged (Gigapack II XL kit, from Stratagene) and plated using E.Coli strain P2392. Plaque lifts were hybridized to radiolabelled human genomic DNA, and positive plaques were selected for further characterization.

Hybridization Analyses and General Methods

Standard techniques were used with minor modifications. For hybridization analyses, aliquots of DNA (1–10 ug) were digested with restriction enzymes, separated by electrophoresis in agarose gels, and transferred to nylon membranes by alkaline blotting. Appropriate controls were included in each experiment. The labelling of probes with $^{32}$P was done by random hexanucleotide priming using a oligo labeling kit (from Pharmacia). Hybridization was carried out in 1M NaCl, 1% sodium dodecyl sulphate (SDS), 10% dextran sulphate, and filters were washed at a high stringency (final washes in 0.1–0.2XSSC, 0.1% SDS at 65° C.) before autoradiography.

Characterization of Somatic Cell Hybrid Clones from patient "AK"

To facilitate mapping of the X chromosomal breakpoint, somatic cell hybrids were constructed by fusing fibroblasts from patient "AK" to rodent cells. In the initial PCR characterization of selected somatic cell hybrids, one clone, AKRAG9, tested negative for DXS159 but positive for CCG1. To rule out gross rearrangements in AKRAG9, ten additional STS's specific for genes from different parts of Xp and Xq were tested (not shown; Kere et al. 1992). The results indicated that AKRAG9 retained the der(1) chromosome including Xq13.1-qter, but neither the der(X) nor the structurally normal X chromosome. These results showed the utility of AKRAG9 DNA for mapping the X chromosomal breakpoint in patient "AK".

Mapping of "AK" Breakpoint Between Loci Closely Linked to EDA

Probes and PCR primers for loci tightly linked to EDA were used to map the breakpoint in AKRAG9 DNA (FIG. 1). FIG. 1 shows mapping of the X chromosomal breakpoint in patient "AK" using previously localized markers tightly linked to the EDA locus. Left, schematic representation of the X chromosome showing the approximate location of the EDA gene in Xq12-q13. Right, mapping of the breakpoint by hybridization (DXS469 to DXS348) or by PCR (DXS453). The asterisk indicates the localization of the translocation breakpoint; the proximal portion of Xq is absent from ADRAG9 whereas the distal portion is retained (lane 1 in all panels). Reference numeral 1 represents AKRAG9 DNA; reference numeral 2 represents "AK" genomic DNA; reference numeral 3 represents DNA from a healthy female; reference numeral 4 represents X only somatic cell hybrid DNA (a positive control); and reference numeral 5 represents X3000 somatic cell hybrid DNA (including Xq24-qter, a negative control).

The results placed the breakpoint distal to DXS469, DXS132, DXS135, and DXS339, and proximal to DXS453 and DXS348. The same interval has been implicated in patient "AnLy" whose breakpoint has previously been mapped distal to DXS159, DXS132, DXS135, and DXS339, and proximal to DXS453, DXS348, and PGK1 (Hanauer et al. 1988; Zonana et al. 1988; Jones et al. 1991; N. Thomas et al., 3rd X Chromosome Workshop abstracts).

Construction of a YAC Contig Spanning Two Translocation Breakpoints by Chromosome Walking Construction of a YAC contig and mapping of the breakpoints in both patients then proceeded in parallel using chromosome walking techniques. Chromosome walking is used in mapping studies to clone adjacent DNA segments and intact chromosomal DNA. It provides ordered selection of a number of overlapping recombinants so that the sequences present in the insert DNAs are cloned in the order in which they occur along the chromosomal DNA. In chromosomal walking, a fragment representing one end of a long piece of DNA is used to isolate another that overlaps and extends the first. The direction of extension is determined by restriction mapping, and the procedure is repeated sequentially until the desired sequence is obtained. The X chromosome-linked disorders are particularly amenable to this type of mapping. Only a single allele is expressed in X-linked disorders, so 20% of the defined RFLPs are on the X chromosome, and a reasonably complete linkage map of the chromosome exists.

Figure 2:
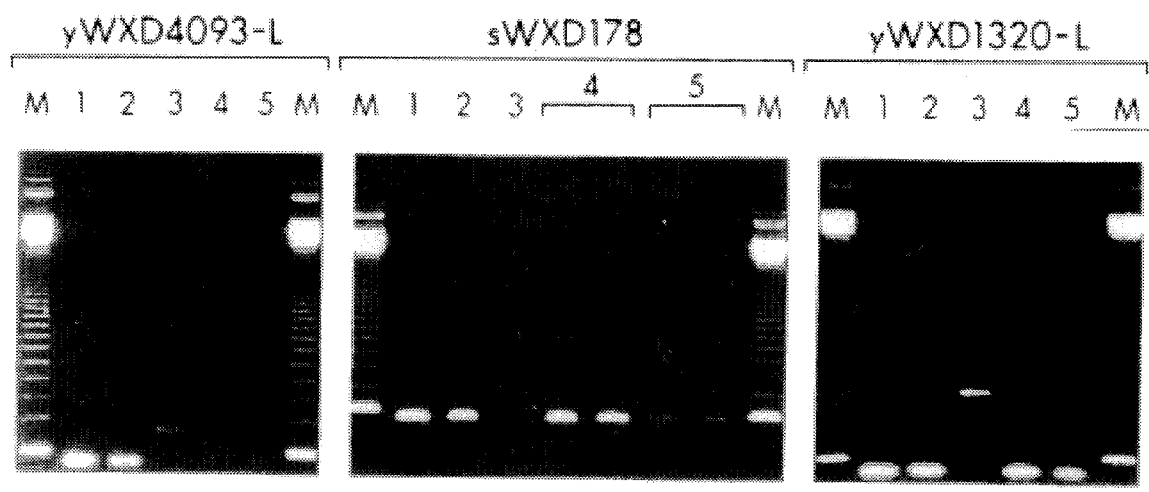
FIG. 2 illustrates identification of a DNA segment between the translocation breakpoints in two patients.

YACs were recovered for DXS339, DXS348, and DXS453, and were assumed to be the loci closest to the breakpoints (Lafreniere et al. 1991; Jones et al. 1991; N. Thomas et al., 3rd X Chromosome Workshop abstracts). Insert ends of several YACs were isolated by ligation-medicated PCR, and an STS for the left insert end of YAC yWXD4093 was used to screen for new YACs and also to map its location in respect to the breakpoints in patients "AK" and "AnLy" (whose DNA was available as a somatic cell hybrid ALR-1-BSH-6, Shows and Brown 1975). FIG. 2 illustrates identification of a DNA segment between the translocation breakpoints in patients "AK" and "AnLy". "AK" and "AnLy". Probe yWXD4093-L is present in neither of the hybrid cells, whereas yWXD1320-L is present in both of them. Probe sWXD178 is present in AKRAG9 DNA but not in ALR-1-BSH-6 DNA. A weak positive band is present in ALR-1-BSH-6 DNA due to the presence of a normal X chromosome in approximately 10% of hybrid cells; the result was confirmed by hybridization using a single-copy probe derived from one end of lambda36/1320 containing sWXD178 (not shown). Reference numeral 1 represents human genomic DNA; reference numeral 2 represents X only somatic cell hybrid cell DNA; reference numeral 3 represents X3000 hybrid cell DNA (Xq24-qter); reference numeral 4 represents AKRAG9 DNA (Xq13-qter; from patient "AK"); reference numeral 5 represents ALR-1-BSH-6 DNA (Xq13-qter; from patient "AnLy"); and M represents molecular size marker (123 bp ladder).

Clone yWXD1320 was identified with this STS which mapped proximal to the breakpoints in both patients (FIG. 2). However, the left insert end-fragment of yWXD1320 mapped distal of the breakpoints in both patients (FIG. 2) and identified six new YACs (Table 1). YAC yWXD1320 and three additional YACs had also been identified by sWXD178 in the process of STS/YAC mapping of the X chromosome.

The YACs and DNA markers incorporated in the YAC contigs are summarized in Tables 1 and 2. Two contigs were constructed, one of about 1.2Mb spanning from DXS135 to markers distal of DXS339 and covering both translocation breakpoints, and another of about 0.3 Mb including DXS453 and DXS348 and mapping distal to both breakpoints.

The presence of DNA markers in yeast artificial chromosome clones forming two contigs. Plus (+) indicates the presence of markers in YACs, and minuses (−) have been omitted for clarity; a period indicates the material was not tested. Characteristics of isolated YAC insert end sequences are as follows: X, unique human X chromosomal sequence; re, human repeated sequence; ch, chimeric end (other than human X chromosomal sequence). The order of the markers is from centromere (to the left) to Xq telomere (to the right). Most YACs smaller than 200 kb have been omitted from the table. The empty column indicates a gap between two YAC contigs.

While it is expected that the vector can express the human EDA gene in skin cell cultures, it is not known whether all types of skin cells will effectively express the gene. It is anticipated, however, that cells such as fibroblasts and keratinocytes can be used for this purpose, since they express the putative gene transcript.

TABLE 1

| YAC NAME | YAC SIZE (kb) | INSERT ENDS LEFT--RIGHT | | DXS135 | yWXD 1319-L | DXS339 |
| --- | --- | --- | --- | --- | --- | --- |
| yWXD5072 | 270 | | ch | + | . | + |
| yWXD4507 | 220 | | | | . | + |
| yWXD4936 | 130 | | | | | + |
| yWXD4895 | 260 | | | | . | + |
| yWXD1317 | 260 | re | | | . | + |
| yWXD1318 | 230 | | | | | + |
| yWXD4093 | 260 | X | | | + | + |
| yWXD1319 | 240 | X | | . | + | + |
| yWXD1320 | 700 | X | | . | + | + |
| yWXD1236 | 300 | | | | . | . |
| yWXD1237 | 310 | ch | | | . | . |
| yWXD1238 | >700 | | | | . | . |
| yWXD3583 | 210 | | | | . | . |
| yWXD1340 | 210 | | | | . | . |
| yWXD1341 | 280 | | | | . | . |
| yWXD1342 | 210 | | | | . | . |
| yWXD1321 | 220 | | | | . | . |
| yWXD5218 | 270 | ch | X | | . | . |
| yWXD1316 | 290 | | | | . | . |

TABLE 2

| YAC NAME | YAC SIZE | yWXD | sWXD | yWXD | DXS453 | yWXD | DXS348 | yWXD |
| --- | --- | --- | --- | --- | --- | --- | --- | --- |
| yWXD5072 | 270 | 4093-L | 178 | 1320-L | | 5218-R | | 1261-R |
| yWXD4507 | 220 | | | | | | | |
| yWXD4936 | 130 | + | | | | | | |
| yWXD4895 | 260 | + | | | | | | |
| yWXD1317 | 260 | + | | | | | | |
| yWXD1318 | 230 | + | | | | | | |
| yWXD4093 | 260 | + | | | | | | |
| yWXD1319 | 240 | + | | | | | | |
| yWXD1320 | 700 | + | + | + | | | | |
| yWXD1236 | 300 | | + | | | | | |
| yWXD1237 | 310 | | + | | | | | |
| yWXD1238 | >700 | | + | + | | | | |
| yWXD3583 | 210 | | | + | | | | |
| yWXD1340 | 210 | | | + | | | | |

TABLE 2-continued

| YAC NAME | YAC SIZE | yWXD | sWXD | yWXD | DXS453 | yWXD | DXS348 | yWXD |
|---|---|---|---|---|---|---|---|---|
| yWXD1341 | 280 | | + | | | | | |
| yWXD1342 | 210 | | + | | | | | |
| yWXD1321 | 220 | | | | + | | | |
| yWXD5218 | 270 | | | | + | + | | |
| yWXD1316 | 290 | | | | + | + | + | + |
| yWXD1261 | 260 | | | | | | + | + |

Identification of Intragenic Markers and Long-range Restriction Mapping of the EDA Gene Region PCR assays on AKRAG9 and ALR-1-BSH-6 DNAs suggested that sWXD178 mapped between the translocation breakpoints (FIG. 2). To confirm this finding and to expand the sWXD178 locus, phage subclone of yWXD1320 was identified that contained sWXD178. An insert end of the clone, lambda36/1320, was isolated by ligation-mediated PCR and used as a hybridization probe. The results confirmed that this locus was present in AKRAG9, but not in ALR-1-BSH-6 DNA (not shown), implicating a more proximal translocation breakpoint in patient "AK" as compared to patient "AnLy". As both translocations supposedly involve parts of the EDA gene, sWXD178 and lambda36/1320 provide intragenic markers.

Figure 3:
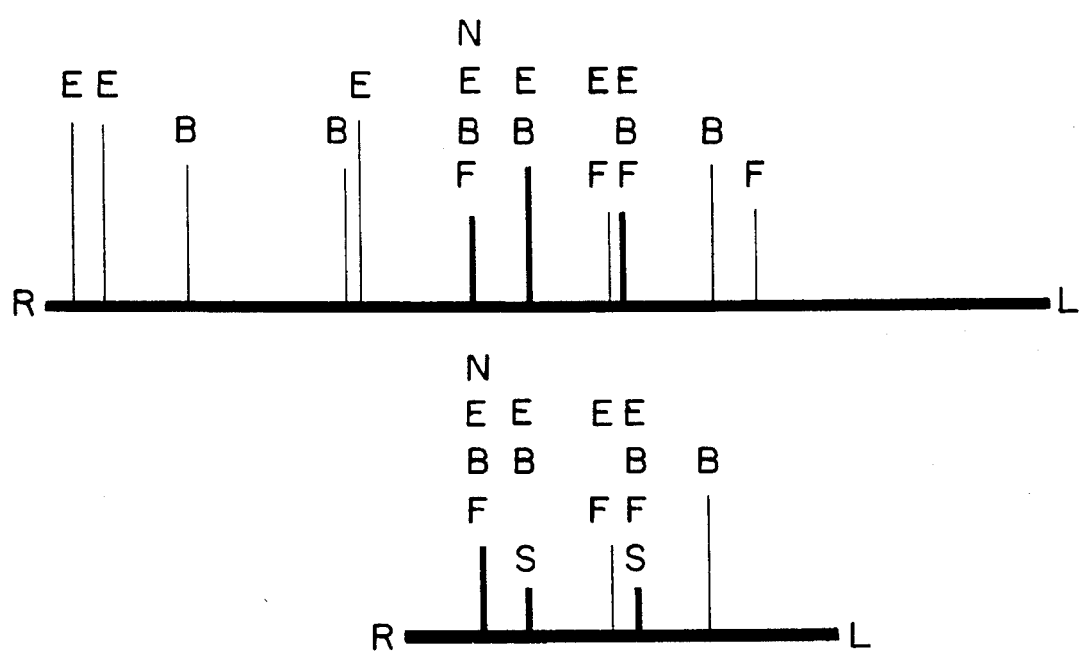
FIG. 3 illustrates long-range restriction maps of YACs yWXD1320 (top) and yWXD1237 (bottom).

Long-range restriction maps for yWXD1320 and yWXD1237 were constructed from total and partial digestions (FIG. 3) and DNA markers were positioned within the YACs. In FIG. 3, the restriction sites are marked as N, NotI; E, EagI; B, BssHII; F, SfiI; and S, SacII. YAC yWXD1237 was mapped with all five enzymes; SacII was not used for yWXD1320. By hybridizing to total digestion and partial digestion PFGE blots, lambda36/1320 was mapped between the BssHII and SfiI sites closest to the left end of yWXD1320 and was also present in yWXD1237. The maps were consistent within the limits of resolution, except that an SfiI site observed closest to the left end in yWXD1320 was not present in yWXD1337. In line with this, the left end of yWXD1237 did not hybridize to yWXD1320, suggesting that yWXD1237-L is a chimeric end. A probe derived from another phage subclone (lambda01/1320) mapped close to the R end of yWXD1237 and was deleted from the AKRAG9 hybrid (not shown). Thus, the translocation breakpoint in "AK" must be within the region covered by yWXD1237.

Figure 4:
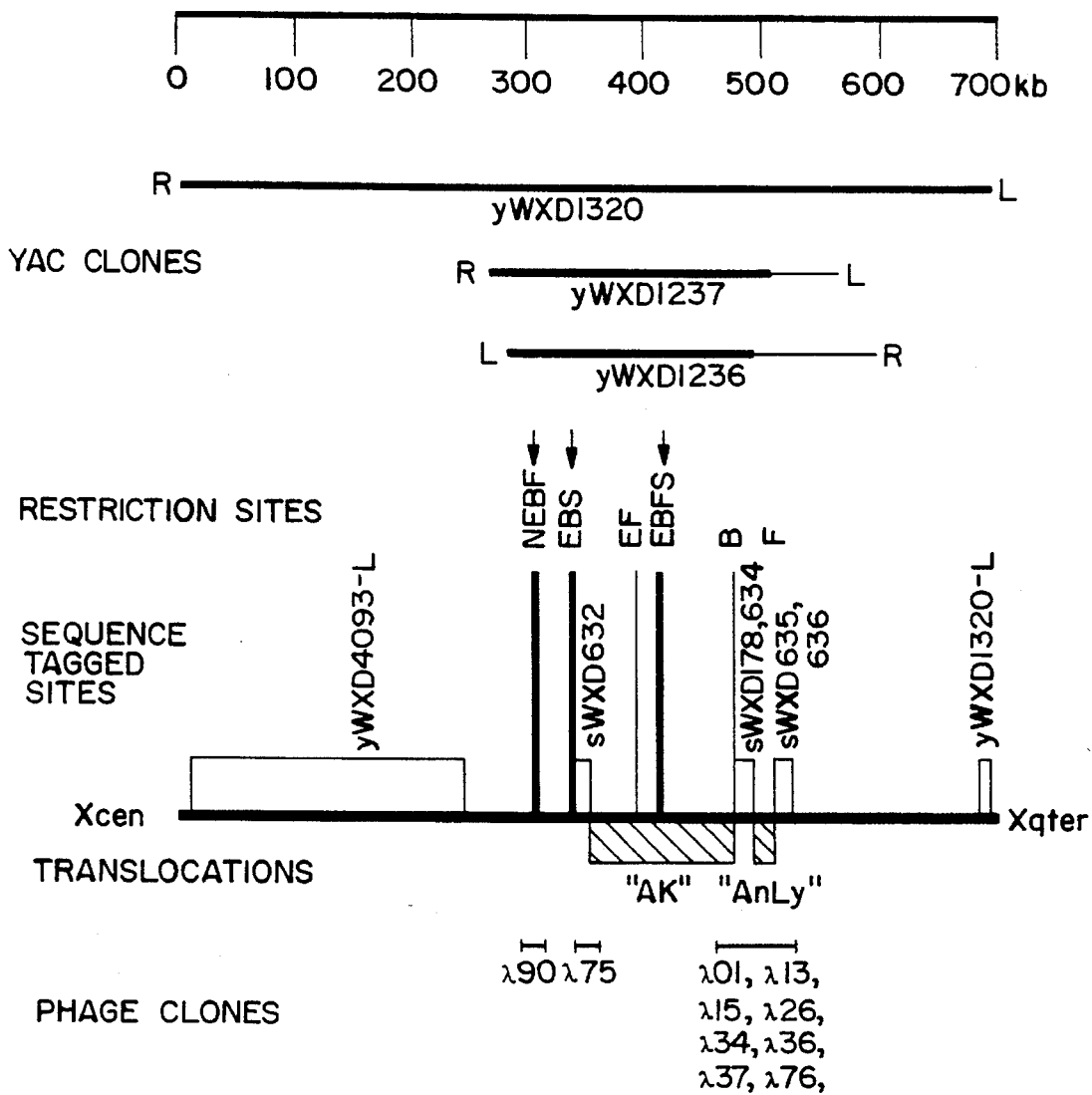
FIG. 4 illustrates a summary map of the EDA gene region.

The summary map of the EDA gene region illustrated in FIG. 4 suggests that the "AK" and "AnLy" breakpoints map within 200 kb, but at least 20 kb apart. Three CpG islands, represented by arrows, were identified which map within 110 kb and reside in the same region as the breakpoint in patient "AK". The CpG islands were identified based on the rare-cutter sites in yWXD1320 and yWXD1237 and are determined as coinciding sites for at least three restriction enzymes used. The "AnLy" breakpoint maps within 50 to 200 kb from these islands in a region where no rare-cutter restriction sites were detected. Stabilization of inactivation is very well correlated with DNA methylation (at the cytosine of a CpG-dinucleotide), which occurs at CpG-rich regions (CpG-islands) near the 5' end of many genes. This feature is useful for mapping by pulsed-field gel electrophoresis because restriction enzymes are sensitive to methylation, and as a way to identify expressed genes in cloned regions.

In FIG. 4, the positions of DNA markers are indicated with open boxes; the breakpoint regions in patients "AK" and "AnLy" are marked as cross-hatched boxes. Additional novel sequences that have been identified, including the following primer sequences:

a) GGCAGTTCCAGTAAAATGCAGAC (SEQ ID NO: 9);
b) GGAGCTGAGGCCAAGGAG (SEQ ID NO: 10);
c) GCTGCAAAATTATTGTTGCTGTGG (SEQ ID NO: 11);
d) AACAAGATCGTGAAACAGGATG (SEQ ID NO: 12);
e) GGTTGTATGGCCTTAGACTC (SEQ ID NO: 13);
f) GTGGTGCTGGGGAATAGTG (SEQ ID NO: 14);
g) TCTGTCCTCTCCTGCCATC (SEQ ID NO: 15);
h) AATAAAGCCTCCTGCCTCCTG (SEQ ID NO: 16);
i) ATTTCCTACCACTCCACCC (SEQ ID NO: 17);
j) CTTGAGATTTGAAGAGAGCCC (SEQ ID NO: 18);
k) ACCACTCCACCCCTTATTC (SEQ ID NO: 19);
l) GACAGAGGTATCAGAAAGTCAAA (SEQ ID NO: 20);
m) CCAGACCTATGAATGCAAAC (SEQ ID NO: 21); and
n) GTGAATAATAGCACTTCTGCC (SEQ ID NO: 22)

are associated with new unique markers labelled sWXD632, sWXD178, sWXD634, sWXD635 and sWXD636. Phage clones λ90, λ75, λ01, λ13, λ15, λ26, λ34, λ36 (lambda36/1320), λ37 and λ76 represent actual fragments of the inventive YACs. The orientation of the X chromosome is indicated ("cen" represents the centromere and "ter" represents the Xq telomere). Based on the map in FIG. 4, it is believed that the 5' end of the EDA gene is associated with one of the CpG islands and the 3' end extends toward the telomere. The "AK" breakpoint would map closer to the 5' end and the "AnLy" breakpoint closer to the 3' end of the gene. The isolated DNA fragments mapping between translocation breakpoints should represent portions of the EDA gene, since the gene is likely to be interrupted in both patients. Thus, sWXD632, sWXD178, sWXD634, sWXD635, sWXD636, λ90, λ75, λ01, λ13, λ15, λ26, λ34, λ36 (lambda36/1320), λ37 and λ76, among others listed above, are intragenic markers for the EDA gene. The translocations will further facilitate both the detection and the verification of the coding regions of the EDA gene, and much testing of candidate genes across the YAC contigs can be bypassed. The presence of several closely located CpG islands (FIGS. 3 and 4) suggests that the region may contain many clustered genes.

Identification of a Tissue-Specific Transcript Encoded by the EDA Region, and Diagnosis of EDA Using portions subcloned at intervals from across the region included in the YACs, a transcript about 9 kb in size has been detected in RNA preparations by Northern analysis (that is, hybridization to filters bearing gel-fractionated RNA species). This transcript has the characteristics expected for the mRNA encoding the product of the EDA gene:

1. It is expressed in keratinocytes and fibroblasts, cells in which EDA expression is expected, but not in a blood cell line.

2. It is detected by probes which flank the two translocation breakpoints, so that it is being encoded across the entire region defining the body of the gene.

3. A species of approximately the same size is detected in a cDNA library constructed from RNA of fibroblasts.

Availability of the DNA as a specific probe, and isolation of the cDNA species as a second specific probe, would allow for the diagnosis of the disease as well as the study of the product of the gene. Deoxyribonucleotide tracts from cells of patients can be analyzed, for example, by Southern blot hybridization or sequencing to detect disruption or modification of the human EDA gene which codes for anhidrotic ectodermal dysplasia.

Diagnosis of Diseases Associated with the X-linked EDA Gene

Specific probes for the newly discovered gene may now be used for the diagnosis of disease states associated therewith. DNA from cells collected may be analyzed by various methods, such as those using various labels as well as by the Southern blot hybridization technique. Exemplary labels include RIA, EIA, and ELISA labels using techniques well known in the art.

Southern blot hybridization is a technique for creating a restriction map of a DNA segment by transferring its restriction subfragments from an agarose gel to a special membrane and then hybridizing the DNA fragments to a specific probe. In this procedure, restriction fragments produced by enzyme digestion of whole DNA are electrophoretically separated according to fragment length on an agarose gel. Resulting size-separated nucleic acids are then blotted onto a filter by a transfer process, such as pressure or electrophoretically passing a high salt buffer through the agarose gel from a buffer-saturated paper wick. The blotted nucleic acids are then hybridized to a probe in a solution containing denaturant and blocking agents which saturate the filter to prevent nonspecific binding of the probe to the filter. Unbound probe is washed off the filter, leaving only the probe specifically hybridized to the filter-bound target sequences (the restriction fragment containing the sequences of interest). For radioactive probes, the signal corresponding to the location of the hybridized probe is visualized by placing x-ray film over the filter (autoradiography). DNA representing as little as $10^{-13}$ g of the target sequences can be detected by this procedure.

Southern blot analysis can be used to diagnose genetic diseases by determining alterations in gene structure that are related to genetic disease, such as mutation or rearrangement of sequences. Thus, using an inventive probe covering the EDA gene region, the presence of the EDA gene can be detected by Southern blot analysis.

Nucleic acid probes are chemically labeled with compounds that allow their presence to be detected following hybridization. A preferred embodiment of the invention provides for cDNA probes. Novel probes of the invention can be produced by other methods, including but not limited to Nick Translation, labeling random primer probes, synthesizing oligonucleotides of the sequence coding for human EDA gene and producing RNA probes.

cDNA probes are DNA strands complementary to an RNA template. Such probes can be synthesized by using the enzyme reverse transcriptase in a reaction mixture containing a RNA template annealed to a short primer strand, four deoxyribonucleoside triphosphates and a magnesium-containing buffer. Labeled DNA probes produced by using labeled deoxyribonucleotides in the reaction mixture can be used as specific probes for any given RNA or population of RNAs. cDNAs can be subjected to restriction digestion, allowing subfragments representing only a specific region of an RNA to be used as a probe.

Nick Translation involves treating double-stranded DNA with DNase I to produce short, randomly placed single-stranded nicks. The nicked regions are simultaneously filled by DNA polymerase I using labeled deoxyribonucleotide triphosphates and the intact strand is then used as a template.

Labeling random primer probes is a variation on nick Translation. A mixture of primers is used to initiate synthesis on single-stranded templates. The random primers are annealed to denatured DNA to form short double-stranded regions separated by long stretches of single-stranded DNA. The single-stranded regions are then filled in using DNA polymerase I and dNTPs in the same way that DNase I-produced gaps are filled in during nick translation.

Oligonucleotides of any specific sequence can be synthesized by adding nucleotides sequentially to the 5' end of an oligonucleotide by (1) deprotection of the 5' end of the growing oligonucleotide in an acidified organic solution, (2) coupling an activated 3' phosphoramidite (a chemically modified nucleotide containing an activated phosphoester group at the 3' carbon and chemically blocked from reaction at the 5' end) to the deprotected 5' end of the oligonucleotide, (3) reblocking any oligonucleotide 5' ends that were not reacted with the phosphoramidite in step 2, (4) oxidizing the phosphorus to the pentavalent state, (5) repeating steps 1 through 4 until the desired full-length oligonucleotide is achieved, and (6) employing alkaline treatment to cleave the cyanoethyl groups attached to the phosphodiester bonds linking the individual nucleotides and hydrolyzing the terminal 3' ester bond to release the oligonucleotide.

RNA probes are long probes specific to only one of two DNA strands. RNA probes may be synthesized by deriving labeled RNAs representing the transcript of an appropriate DNA strand using bacterial RNA polymerase in the presence of the labeled ribonucleotide triphosphates.

The novel probes of the invention can be labeled by any conventional probe labeling technique, such as radioactive labeling and nonradioactive labeling. Nonradioactive labeling techniques useful in the invention include but are not limited to covalently binding chromogenic compounds (such as ethidium, dinitrophenol, fluorescein, tetramethyl rhodamine and nitrobenzofuran) to purine or pyrimidine base; covalently binding molecules, such as enzymes, to a probe to generate colored products using synthetic substrates; covalently attaching happens to purines or pyrimidines which can then be bound by a labeled ligand (hapten-ligand binding); antibody-linked labeling, such as chromogen-conjugated antibodies to haptens bound to DNA (small organic molecules such as N-2-acetylaminofluorene, dinitrophenyl and ethidium are coupled to purine and pyrimidine bases and then antibody techniques are applied); peroxidase labeling (for example, horseradish peroxidase); pyrimidine-adducted alkaline phosphatase used in combination with a variety of chromogenic substrate; and biotin-avidin labeling.

Using fragments of the various yeast artificial chromosomes described above as probes specific for X-linked anhidrotic ectodermal dysplasia, a kit for diagnosis can be prepared, comprising a probe specific for diseases associated with the X-linked anhidrotic ectodermal dysplasia gene. More specifically, a kit for diagnosing EDA gene-linked diseases can be prepared, comprising a cloning vector containing all or a portion of a DNA sequence encoding human EDA gene.

More particularly, a method of diagnosing disease caused by the X-linked EDA gene comprises:

a) obtaining a sample of cells;

b) contacting the cells with a detectable material which links to the X-linked EDA gene; and c) determining the presence or absence of a disease affecting tissues selected from the group consisting of hair, skin, teeth, and sweat glands.

A kit for the diagnosis of X-linked EDA gene diseases may comprise a probe specific for the X-linked EDA gene and a label for the probe to enable detection of the same. The kit may also contain an RIA, EIA, or ELISA label.

The probe specific for the EDA gene is preferably at least a fragment of a yeast artificial chromosome which is cloned in a vector selected from the group consisting of a bacteriophage and a cosmid. Alternatively, the probe is obtained by amplifying the DNA fragment of the EDA gene.

The invention being thus described, it will be obvious that the same may be varied in many ways. Such variations are not to be regarded as a departure from the spirit and scope of the invention, and also such modifications are intended to be included within the scope of the following claims.

We claim:

1. A cloning vector comprising a DNA sequence of the human anhydrotic ectodermal dysplasia (EDA) gene, wherein an RNA preparation of said vector is capable of expressing human EDA gene product in skin cell culture.

2. The vector of claim 1, wherein said vector is a yeast artificial chromosome.

3. The vector of claim 1, wherein said vector is a plasmid. Clones yWXD1320, yWXD1236, and yWXD1237 have been deposited with the American Type Culture Collection, 12301 Parklawn Drive, Rockville, Md. 20852, and assigned ATCC accession numbers 80369, 80896, and 80272, respectively.

4. A purified and isolated DNA fragment comprising a DNA sequence encoding human EDA gene.

5. A purified and isolated DNA fragment comprising a nucleotide sequence complementary to a sequence selected from the group consisting of:

a) GGCAGTTCCAGTAAAATGCAGAC (SEQ ID NO: 9);

b) GGAGCTGAGGCCAAGGAG (SEQ ID NO: 10);

c) GCTGCAAAATTATTGTTGCTGTGG (SEQ ID NO: 11);

d) AACAAGATCGTGAAACAGGATG (SEQ ID NO: 12);

e) GGTTGTATGGCCTTAGACTC (SEQ ID NO: 13);

f) GTGGTGCTGGGGAATAGTG (SEQ ID NO: 14);

g) TCTGTCCTCTCCTGCCATC (SEQ ID NO: 15);

h) AATAAAGCCTCCTGCCTCCTG (SEQ ID NO: 16);

i) ATTTCCTACCACTCCACCC (SEQ ID NO: 17);

j) CTTGAGATTTGAAGAGAGCCC (SEQ ID NO: 21);

k) ACCACTCCACCCCTTATTC (SEQ ID NO: 19);

l) GACAGAGGTATCAGAAAGTCAAA (SEQ ID NO: 20);

m) CCAGACCTATGAATGCAAAC (SEQ ID NO: 21); and n) GTGAATAATAGCACTTCTGCC (SEQ ID NO: 22).

* * * * *

SEQUENCE LISTING ( 1 ) GENERAL INFORMATION:

( i i i ) NUMBER OF SEQUENCES: 22

( 2 ) INFORMATION FOR SEQ ID NO:1:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: unknown ( i i ) MOLECULE TYPE: DNA (genomic)

( i i i ) HYPOTHETICAL: NO ( v i ) ORIGINAL SOURCE:
        ( A ) ORGANISM: Homo sapiens ( v i i ) IMMEDIATE SOURCE:
        ( B ) CLONE: Yeast Artificial Chromosome ( x i ) SEQUENCE DESCRIPTION: SEQ ID NO:1:

GTTAATAGTA ATGTCCTCTC TTTC      24

( 2 ) INFORMATION FOR SEQ ID NO:2:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: unknown ( i i ) MOLECULE TYPE: DNA (genomic)

( i i i ) HYPOTHETICAL: NO ( v i ) ORIGINAL SOURCE:
        ( A ) ORGANISM: Homo sapiens ( v i i ) IMMEDIATE SOURCE:
        ( B ) CLONE: yeast artificial chromosome ( x i ) SEQUENCE DESCRIPTION: SEQ ID NO:2:

ACCTTTAGTT AGATTGATGA AGCC      24

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: unknown ( i i ) MOLECULE TYPE: DNA (genomic)

( i i i ) HYPOTHETICAL: NO ( v i ) ORIGINAL SOURCE:

17

-continued ( A ) ORGANISM: Homo sapiens ( v i i ) IMMEDIATE SOURCE:
        ( B ) CLONE: yeast artificial chromosome ( x i ) SEQUENCE DESCRIPTION: SEQ ID NO:3:

CAAGGAAAGG GATTGGCAAG        20

( 2 ) INFORMATION FOR SEQ ID NO:4:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: unknown ( i i ) MOLECULE TYPE: DNA (genomic)

( i i i ) HYPOTHETICAL: NO ( v i ) ORIGINAL SOURCE:
    ( A ) ORGANISM: Homo sapiens ( v i i ) IMMEDIATE SOURCE:
    ( B ) CLONE: yeast artificial chromosome ( x i ) SEQUENCE DESCRIPTION: SEQ ID NO:4:

AGACCCGAGA GAGCAATTAG        20

( 2 ) INFORMATION FOR SEQ ID NO:5:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: unknown ( i i ) MOLECULE TYPE: DNA (genomic)

( i i i ) HYPOTHETICAL: NO ( v i ) ORIGINAL SOURCE:
    ( A ) ORGANISM: Homo sapiens ( v i i ) IMMEDIATE SOURCE:
    ( B ) CLONE: yeast artificial chromosome ( x i ) SEQUENCE DESCRIPTION: SEQ ID NO:5:

GAACAGGTTA TGGGAGGGG        19

( 2 ) INFORMATION FOR SEQ ID NO:6:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: unknown ( i i ) MOLECULE TYPE: DNA (genomic)

( i i i ) HYPOTHETICAL: NO ( v i ) ORIGINAL SOURCE:
    ( A ) ORGANISM: Homo sapiens ( v i i ) IMMEDIATE SOURCE:
    ( B ) CLONE: yeast artificial chromosome ( x i ) SEQUENCE DESCRIPTION: SEQ ID NO:6:

GATCTGGAAA GATGAGCTGA G        21

( 2 ) INFORMATION FOR SEQ ID NO:7:

(i) SEQUENCE CHARACTERISTICS:
  (A) LENGTH: 22 base pairs
  (B) TYPE: nucleic acid
  (C) STRANDEDNESS: single
  (D) TOPOLOGY: unknown (ii) MOLECULE TYPE: DNA (genomic)

(iii) HYPOTHETICAL: NO (vi) ORIGINAL SOURCE:
  (A) ORGANISM: Homo sapiens (vii) IMMEDIATE SOURCE:
  (B) CLONE: yeast artificial chromosome (xi) SEQUENCE DESCRIPTION: SEQ ID NO:7:

TCTTGTATCC CTTTGCTTAC TG                    22

(2) INFORMATION FOR SEQ ID NO:8:

(i) SEQUENCE CHARACTERISTICS:
    (A) LENGTH: 24 base pairs
    (B) TYPE: nucleic acid
    (C) STRANDEDNESS: single
    (D) TOPOLOGY: unknown (ii) MOLECULE TYPE: DNA (genomic)

(iii) HYPOTHETICAL: NO (vi) ORIGINAL SOURCE:
    (A) ORGANISM: Homo sapiens (vii) IMMEDIATE SOURCE:
    (B) CLONE: yeast artificial chromosome (xi) SEQUENCE DESCRIPTION: SEQ ID NO:8:

CATTTGCCCA ACTTACTAAA CCAC                  24

(2) INFORMATION FOR SEQ ID NO:9:

(i) SEQUENCE CHARACTERISTICS:
    (A) LENGTH: 23 base pairs
    (B) TYPE: nucleic acid
    (C) STRANDEDNESS: single
    (D) TOPOLOGY: unknown (ii) MOLECULE TYPE: DNA (genomic)

(iii) HYPOTHETICAL: NO (vi) ORIGINAL SOURCE:
    (A) ORGANISM: Homo sapiens (vii) IMMEDIATE SOURCE:
    (B) CLONE: yeast artificial chromosome (xi) SEQUENCE DESCRIPTION: SEQ ID NO:9:

GGCAGTTCCA GTAAAATGCA GAC                   23

(2) INFORMATION FOR SEQ ID NO:10:

(i) SEQUENCE CHARACTERISTICS:
    (A) LENGTH: 18 base pairs
    (B) TYPE: nucleic acid
    (C) STRANDEDNESS: single
    (D) TOPOLOGY: unknown (ii) MOLECULE TYPE: DNA (genomic)

(iii) HYPOTHETICAL: NO (v i) ORIGINAL SOURCE:
    (A) ORGANISM: Homo sapiens (v i i) IMMEDIATE SOURCE:
    (B) CLONE: yeast artificial chromosome (x i) SEQUENCE DESCRIPTION: SEQ ID NO:10:

GGAGCTGAGG CCAAGGAG                                                             18

(2) INFORMATION FOR SEQ ID NO:11:

(i) SEQUENCE CHARACTERISTICS:
        (A) LENGTH: 24 base pairs
        (B) TYPE: nucleic acid
        (C) STRANDEDNESS: single
        (D) TOPOLOGY: unknown (i i) MOLECULE TYPE: DNA (genomic)

(i i i) HYPOTHETICAL: NO (v i) ORIGINAL SOURCE:
        (A) ORGANISM: Homo sapiens (v i i) IMMEDIATE SOURCE:
        (B) CLONE: yeast artificial chromosome (x i) SEQUENCE DESCRIPTION: SEQ ID NO:11:

GCTGCAAAAT TATTGTTGCT GTGG                                                      24

(2) INFORMATION FOR SEQ ID NO:12:

(i) SEQUENCE CHARACTERISTICS:
        (A) LENGTH: 22 base pairs
        (B) TYPE: nucleic acid
        (C) STRANDEDNESS: single
        (D) TOPOLOGY: unknown (i i) MOLECULE TYPE: DNA (genomic)

(i i i) HYPOTHETICAL: NO (v i) ORIGINAL SOURCE:
        (A) ORGANISM: Homo sapiens (v i i) IMMEDIATE SOURCE:
        (B) CLONE: yeast artificial chromosome (x i) SEQUENCE DESCRIPTION: SEQ ID NO:12:

AACAAGATCG TGAAACAGGA TG                                                        22

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: unknown (i i) MOLECULE TYPE: DNA (genomic)

(i i i) HYPOTHETICAL: NO (v i) ORIGINAL SOURCE:
        (A) ORGANISM: Homo sapiens (v i i) IMMEDIATE SOURCE:
        (B) CLONE: yeast artificial chromosome (x i) SEQUENCE DESCRIPTION: SEQ ID NO:13:

GGTTGTATGG CCTTAGACTC                                                           20

( 2 ) INFORMATION FOR SEQ ID NO:14:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: unknown ( i i ) MOLECULE TYPE: DNA (genomic)

( i i i ) HYPOTHETICAL: NO ( v i ) ORIGINAL SOURCE:
        ( A ) ORGANISM: Homo sapiens ( v i i ) IMMEDIATE SOURCE:
        ( B ) CLONE: yeast artificial chromosome ( x i ) SEQUENCE DESCRIPTION: SEQ ID NO:14:

GTGGTGCTGG GGAATAGTG        19

( 2 ) INFORMATION FOR SEQ ID NO:15:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: unknown ( i i ) MOLECULE TYPE: DNA (genomic)

( i i i ) HYPOTHETICAL: NO ( v i ) ORIGINAL SOURCE:
        ( A ) ORGANISM: Homo sapiens ( v i i ) IMMEDIATE SOURCE:
        ( B ) CLONE: yeast artificial chromosome ( x i ) SEQUENCE DESCRIPTION: SEQ ID NO:15:

TCTGTCCTCT CCTGCCATC        19

( 2 ) INFORMATION FOR SEQ ID NO:16:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: unknown ( i i ) MOLECULE TYPE: DNA (genomic)

( i i i ) HYPOTHETICAL: NO ( v i ) ORIGINAL SOURCE:
        ( A ) ORGANISM: Homo sapiens ( v i i ) IMMEDIATE SOURCE:
        ( B ) CLONE: yeast artificial chromosome ( x i ) SEQUENCE DESCRIPTION: SEQ ID NO:16:

AATAAAGCCT CCTGCCTCCTG        21

( 2 ) INFORMATION FOR SEQ ID NO:17:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: unknown ( i i ) MOLECULE TYPE: DNA (genomic)

( i i i ) HYPOTHETICAL: NO ( v i ) ORIGINAL SOURCE:
    ( A ) ORGANISM: Homo sapiens ( v i i ) IMMEDIATE SOURCE:
    ( B ) CLONE: yeast artificial chromosome ( x i ) SEQUENCE DESCRIPTION: SEQ ID NO:17:

ATTTCCTACC ACTCCACCC  19

( 2 ) INFORMATION FOR SEQ ID NO:18:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: unknown ( i i ) MOLECULE TYPE: DNA (genomic)

( i i i ) HYPOTHETICAL: NO ( v i ) ORIGINAL SOURCE:
        ( A ) ORGANISM: Homo sapiens ( v i i ) IMMEDIATE SOURCE:
        ( B ) CLONE: yeast artificial chromosome ( x i ) SEQUENCE DESCRIPTION: SEQ ID NO:18:

CTTGAGATTT GAAGAGAGCCC  21

( 2 ) INFORMATION FOR SEQ ID NO:19:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: unknown ( i i ) MOLECULE TYPE: DNA (genomic)

( i i i ) HYPOTHETICAL: NO ( v i ) ORIGINAL SOURCE:
        ( A ) ORGANISM: Homo sapiens ( v i i ) IMMEDIATE SOURCE:
        ( B ) CLONE: yeast artificial chromosome ( x i ) SEQUENCE DESCRIPTION: SEQ ID NO:19:

ACCACTCCAC CCCTTATTC  19

( 2 ) INFORMATION FOR SEQ ID NO:20:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: unknown ( i i ) MOLECULE TYPE: DNA (genomic)

( i i i ) HYPOTHETICAL: NO ( v i ) ORIGINAL SOURCE:
        ( A ) ORGANISM: Homo sapiens ( v i i ) IMMEDIATE SOURCE:
        ( B ) CLONE: yeast artificial chromosome ( x i ) SEQUENCE DESCRIPTION: SEQ ID NO:20:

GACAGAGGTA TCAGAAAGTC AAA  23

( 2 ) INFORMATION FOR SEQ ID NO:21:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: unknown ( i i ) MOLECULE TYPE: DNA (genomic)

( i i i ) HYPOTHETICAL: NO ( v i ) ORIGINAL SOURCE:
        ( A ) ORGANISM: Homo sapiens ( v i i ) IMMEDIATE SOURCE:
        ( B ) CLONE: yeast artificial chromosome ( x i ) SEQUENCE DESCRIPTION: SEQ ID NO:21:

CCAGACCTAT GAATGCAAAC     20

( 2 ) INFORMATION FOR SEQ ID NO:22:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: unknown ( i i ) MOLECULE TYPE: DNA (genomic)

( i i i ) HYPOTHETICAL: NO ( v i ) ORIGINAL SOURCE:
        ( A ) ORGANISM: Homo sapiens ( v i i ) IMMEDIATE SOURCE:
        ( B ) CLONE: yeast artificial chromosome ( x i ) SEQUENCE DESCRIPTION: SEQ ID NO:22:

GTGAATAATA GCACTTCTGC C     21